United States Patent [19]
Bennett et al.

[11] Patent Number: 6,127,606
[45] Date of Patent: *Oct. 3, 2000

[54] METHOD OF USING TRANSACTIVATION PROTEINS TO CONTROL EXPRESSION IN TRANSGENIC PLANTS

[75] Inventors: Malcolm Bennett, Coventry; Sean May, Earlsdon; Nicola Ramsay, Bishopston, all of United Kingdom

[73] Assignee: University of Warwick, Coventry, United Kingdom

[*] Notice: This patent is subject to a terminal disclaimer.

[21] Appl. No.: 09/123,644

[22] Filed: Jul. 28, 1998

Related U.S. Application Data

[63] Continuation-in-part of application No. 08/452,267, May 26, 1995, Pat. No. 5,801,027.

[30] Foreign Application Priority Data

Feb. 8, 1995 [GB] United Kingdom ............... 9502456

[51] Int. Cl.$^7$ ...................... C12N 15/00; C12N 15/29; C12N 15/82; A01H 5/00; A01H 4/00

[52] U.S. Cl. ................ 800/298; 800/295; 800/278; 536/24.1; 536/23.6; 536/23.7; 435/320.1; 435/468; 435/419

[58] Field of Search ............................. 435/419, 320.1, 435/468; 800/278, 295, 298; 536/24.1, 23.6, 23.7

[56] References Cited

U.S. PATENT DOCUMENTS

| | | | |
|---|---|---|---|
| 5,409,823 | 4/1995 | Crossland et al. | 435/172.3 |
| 5,801,027 | 9/1998 | Bennett et al. | 435/172.3 |

FOREIGN PATENT DOCUMENTS

| | | |
|---|---|---|
| 2150039 | 8/1996 | Canada . |
| WO92/19747 | 11/1992 | WIPO . |

OTHER PUBLICATIONS

Maas et al. Microbiol. Reviews. vol. 58(4), pp. 631–640, 1994.
University of Warwick, "Farmers could cultivate crops of plastic: New technique opens door to cheap cultivation of plastics in transgenic oilseed rape", Press Release, May 26, 1995.
Koning et al., "Arrest of embryo development in *Brassica napus* mediated by modified *Pseudomonas aeruginosa* exotoxin A", Plant Mol. Biol., vol. 18, pp. 247–258, (1992).
O'Kane et al., "Detection in situ of genomic regulatory elements in Drosophila", PNAS (USA), vol. 84, pp. 9123–9127, (1987).
Johnston, "A Model Fungal Gene Regulatory Mechanism: the GAL GEnes of *Saccharomyces Cerevisiae*", Microbiol. Rev., vol. 51 (4), pp. 458–476 (1987).
Ma et al., "Deletion Analysis of GAL4 Defines Two Transcriptional Activating Segments", Cell, vol. 48, pp. 847–853, (1987).
Brent et al., "A Eukaryotic Transcriptional Activator Bearing the DNA Specificity of a Prokaryotic Repressor", Cell, vol. 43, pp. 729–736, (1985).
West et al, "*Saccharomyces cerecisiae* GAL1–GAL10 Divergent Promoter Region: Location and Function of the Upstream Activating Sequence UAS$_G$", Mol. Cell. Biol., vol. 4 (11), pp. 2467–2478, (1984).
Giniger et al., "Specific DNA Binding of GAL4, A Positive Regulatory Protein of Yeast", Cell, vol. 40, pp. 767–774, (1985).
Lorch et al., "A Region Flanking the GAL7 Gene and a Binding Site for GAL4 Protein as Upstream Activating Sequences in Yeast", J. Mol. Biol., vol. 186, pp. 821–824, (1985).
Keegan et al., "Separation of DNA Binding from the Transcription–Activating Function of a Eukaryotic Regulatory Protein", Sci., vol. 231, pp. 699–704, (1986).
Johnston et al., "Genetic evidence that zinc is an essential co–factor in the DNA binding domain of GAL4 protein", Nature, vol. 328, pp. 353–355, (1987).
Marmorstein et al., "DNA recognition by GAL4: structure of a protein–DNA complex", Nature, vol. 356, pp. 408–414, (1992).
Carey et al., "An Amino–terminal Fragment of GAL4 Binds BNA as a Dimer", J. Mol. Biol. vol. 209, pp. 423–432, (1989).
Silver et al., "Amino terminus of the yeast GAL4 gene product is sufficient for nuclear localization", PNAS (USA), vol. 81, pp. 5951–5955, (1984).
Lin et al., GAL4 Derivatives Function Alone and Synergistically with Mammalian Activation in Vitro, Cell. vol. 54, pp. 659–664, (1988).
Kakidani et al., "GAL4 Activates Gene Expression in Mammalian Cells", Cell. vol. 52, pp. 161–167, (1988).
Webster et al., "The Yeast UAS$_G$ is a Transcriptional Enhancer in Human HeLa Cells in the Presence of the GAL4 Trans–Activator", Cell, vol. 52, pp. 169–178, (1988).
Ma et al., "Yeast activators stimulate plant gene expression", Nature, vol. 334, pp. 631–633, (1988).
Brand et al., "Targeted gene expression as a means of altering cell fates and generating dominate phenotypes", Development, vol. 118, pp. 401–415, (1993).

(List continued on next page.)

*Primary Examiner*—Lynette R. F. Smith
*Assistant Examiner*—Thomas Haas
*Attorney, Agent, or Firm*—Barnes & Thornburg

[57] ABSTRACT

The invention discloses methods of controlling one or more genes in plants. The genes may be exogenous genes and produce a desired phenotypic trait in the plants produced. The genes are operatively linked to a heterologous upstream activating sequence (UAS) recognition site, which is activatable by a transactivating protein. The genes linked to the UAS sequence, and nucleic acid encoding for the transactivating protein may originally be in separate transgenic plants, one of which fertilizes the other to produce reproductive material, such as seed, which may be grown into plants expressing the desired phenotype. The desired phenotype may be herbicide resistance or the production of a polyhydroxyalkanoate, such as polyhydroxybutyrate.

32 Claims, 10 Drawing Sheets

OTHER PUBLICATIONS

Greig et al., "Homeotic genes autonomously specify one aspect of pattern in the *Drosophila mesoderm*", Nature, vol. 362, pp. 630–632, (1993).

Yanisch–Perron et al., "Improved M13 phage cloning vectors and host strains: nucleotide sequences of the M13mp18 an pUC19 vectors", Gene, vol. 33, pp. 103–119, (1985).

Jefferson et al., "GUS fusions: β–glucuronidase as a sensitive and versatile gene fusion marker in higer plants", EMBO J., vol. 6 (13), pp. 3901–3907, (1987).

Odell et al, "Identification of DNA sequences required for activity of the cauliflower mosaic virus 35S promoter", Nature, vol. 313, pp. 810–812, (1985).

Vancanneyt et al., "Construction of an intron–containing marker gene: Splicing of the intron in transgenic plants and its use in monitoring early events in Agrobacterium–mediated plant transformation", Mol.Gen.Gent.,vol. 220,pp. 245–250, (1990).

Weinmann et al., "A chimeric transactivor allows tetracyline–responsive gene expression in whole plants", The Plant Journal, vol. 5(4), pp. 559–569 (1994).

Poirier et al., "Polyhydroxybutyrate, a Biodegradable Thermoplastic, Produced in Transgenic Plants", Science, vol. 256, pp. 520–523 (1992).

Mariani C. et al, "Induction of Male–Sterility in Plants By A Chimeric Ribonnuclease Gene", Nature, vol. 347, pp. 737–741 (1990).

Smith C. J. et al., "Antisense RNA Inhibition of Polygalacturonase Gene–Expression In Transgenic Tomatoes", Nature, vol. 334, pp. 724–726, (1988).

Hamilton A. J. et al., "Antisense Gene That Inhibits Synthesis of the Hormone Ethylene In Transgenic Plants", Nature, vol. 346, pp. 284–287., 1990, (1990).

Zambryski P. et al, "Ti Plasmid Vector for the Introduction of DNA into Plant Cells Without Alteration of Their Normal Regeneration Capacity", EMBO, vol. 2, No. 2, 2143–50, (1983).

Becker, et al., "New Plant Binary Vectors with Selectable Markers Located Proximal to The Left T–DNA Border", Plant Molecular Biology, vol. 20, No. 6, 1195–1197, (1992).

Meyer P. and Saedler H. Ann., "Homology–Dependent Gene Silencing in Plants", Annu. Rev. Plant Physiol. Plant Mol. Biol., vol. 47, pp. 23–48, (1996).

Baulcombe, D.C.; English, James J., Ectopic Pairing of Homologous DNA and Post–Transcriptional Gene Silencing in Transgenic Plants, Curr. Opin. Biotech., vol. 7, No. 2, pp. 173–180, (1996).

ArgF-Gus Bsc

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 980 base pairs
      (B) TYPE: nucleic acid -continued (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Saccharomyces cerevisiae (vii) IMMEDIATE SOURCE:
         (B) CLONE: pGAL4

(xi) SEQUENCE DESCRIPTION: SEQ ID NO:1:

```
CCCGCGATCA GCTTGAAGCA AGCCTCCTGA AAGATGAAGC TACTGTCTTC TATCGAACAA      60

GCATGCGATA TTTGCCGACT TAAAAAGCTC AAGTGCTCCA AAGAAAAACC GAAGTGCGCC     120

AAGTGTCTGA AGAACAACTG GGAGTGTCGC TACTCTCCCA AAACCAAAAG GTCTCCGCTG     180

ACTAGGGCAC ATCTGACAGA AGTGGAATCA AGGCTAGAAA GACTGGAACA GCTATTTCTA     240

CTGATTTTTC CTCGAGAAGA CCTTGACATG ATTTTGAAAA TGGATTCTTT ACAGGATATA     300

AAAGCATTGT TAACAGGATT ATTTGTACAA GATAATGTGA ATAAAGATGC CGTCACAGAT     360

AGATTGGCTT CAGTGGAGAC TGATATGCCT CTAACATTGA GACAGCATAG AATAAGTGCT     420

ACATCATCAT CGGAAGAGAG TAGTAACAAA GGTCAAAGAC AGTTGACTGT ATCGTTCCGG     480

AATTCCGCCA ATTTTAATCA AAGTGGGAAT ATTGCTGATA GCTCATTGTC CTTCACTTTC     540

ACTAACAGTA GCAACGGTCC GAACCTCATA ACAACTCAAA CAAATTCTCA AGCGCTTTCA     600

CAACCAATTG CCTCCTCTAA CGTTCATGAT AACTTCATGA ATAATGAAAT CACGGCTAGT     660

AAAATTGATG ATGGTAATAA TTCAAAACCA CTGTCACCTG GTTGGACGGA CCAAACTGCG     720

TATAACGCGT TTGGAATCAC TACAGGGATG TTTAATACCA CTACAATGGA TGATGTATAT     780

AACTATCTAT TCGATGATGA AGATACCCCA CCAAACCCAA AAAAAGAGTA AAATGAATCG     840

TAGATACTGA AAAACCCCGC AAGTTCACTT CAACTGTGCA TCGTGCACCA TCTCAATTTC     900

TTTCATTTAT ACATCGTTTT GCCTTCTTTT ATGTAACTAT ACTCCTCTAA GTTTCAATCT     960

TGGCCATGTA ACCTCTGATC                                                 980
```

(2) INFORMATION FOR SEQ ID NO:2:

(i) SEQUENCE CHARACTERISTICS:
        (A) LENGTH: 2633 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
         (B) CLONE: pUMIGIT(insert)

(xi) SEQUENCE DESCRIPTION: SEQ ID NO:2:

```
GAGCTCNNNN CCCGGAGGAC AGTACTCCGC CCCCGGAGGA CAGTACTCCG CCCCCGGAGG      60

ACAGTACTCC GCCCCCGGAG GACAGTACTC CGCCCCCGGA GGACAGTACT CCGCCCCCGG     120

AGGACAGTAC TCCGCCCCCG GAGGACAGTA CTCCGCCCCC GGAGGACAGT ACTCCGCCCC     180

CGGAGGACAG TACTCCGCCN NNGGATCCNN NNNCCCGGGN NNNCTGCAGA CTATCCTTCG     240
```

```
CAAGACCCTT CCTCTATATA AGGAAGTTCA TTTCATTYGG AGAGAACAGG ATCCNNNNGG      300

TCAGTCCCTT ATGTTACGTC CTGTAGAAAC CCCAACCCGT GAAATCAAAA AACTCGACGG      360

CCTGTGGGCA TTCAGTCTGG ATCGCGAAAA CTGTGGAATT GATCAGCGTT GGTGGGAAAG      420

CGCGTTACAA GAAAGCCGGG CAATTGCTGT GCCAGGCAGT TTTAACGATC AGTTCGCCGA      480

TGCAGATATT CGTAATTATG CGGGCAACGT CTGGTATCAG CGCGAAGTCT TTATACCGAA      540

AGGTTGGGCA GGCCAGCGTA TCGTGCTGCG TTTCGATGCG GTCACTCATT ACGGCAAAGT      600

GTGGGTCAAT AATCAGGAAG TGATGGAGCA TCAGGGCGGC TATACGCCAT TTGAAGCCGA      660

TGTCACGCCG TATGTTATTG CCGGGAAAAG TGTACGTAAG TTTCTGCTTC TACCTTTGAT      720

ATATATATAA TAATTATCAT TAATTAGTAG TAATATAATA TTTCAAATAT TTTTTTCAAA      780

ATAAAAGAAT GTAGTATATA GCAATTGCTT TTCTGTAGTT TATAAGTGTG TATATTTTAA      840

TTTATAACTT TTCTAATATA TGACCAAAAT TTGTTGATGT GCAGGTATCA CCGTTTGTGT      900

GAACAACGAA CTGAACTGGC AGACTATCCC GCCGGGAATG GTGATTACCG ACGAAAACGG      960

CAAGAAAAAG CAGTCTTACT TCCATGATTT CTTTAACTAT GCCGGAATCC ATCGCAGCGT     1020

AATGCTCTAC ACCACGCCGA ACACCTGGGT GGACGATATC ACCGTGGTGA CGCATGTCGC     1080

GCAAGACTGT AACCACGCGT CTGTTGACTG GCAGGTGGTG GCCAATGGTG ATGTCAGCGT     1140

TGAACTGCGT GATGCGGATC AACAGGTGGT TGCAACTGGA CAAGGCACTA GCGGGACTTT     1200

GCAAGTGGTG AATCCGCACC TCTGGCAACC GGGTGAAGGT TATCTCTATG AACTGTGCGT     1260

CACAGCCAAA AGCCAGACAG AGTGTGATAT CTACCCGCTT CGCGTCGGCA TCCGGTCAGT     1320

GGCAGTGAAG GGCCAACAGT TCCTGATTAA CCACAAACCG TTCTACTTTA CTGGCTTTGG     1380

TCGTCATGAA GATGCGGACT TACGTGGCAA AGGATTCGAT AACGTGCTGA TGGTGCACGA     1440

CCACGCATTA ATGGACTGGA TTGGGGCCAA CTCCTACCGT ACCTCGCATT ACCCTTACGC     1500

TGAAGAGATG CTCGACTGGG CAGATGAACA TGGCATCGTG GTGATTGATG AAACTGCTGC     1560

TGTCGGCTTT AACCTCTCTT TAGGCATTGG TTTCGAAGCG GGCAACAAGC CGAAAGAACT     1620

GTACAGCGAA GAGGCAGTCA ACGGGAAAC TCAGCAAGCG CACTTACAGG CGATTAAAGA     1680

GCTGATAGCG CGTGACAAAA ACCACCCAAG CGTGGTGATG TGGAGTATTG CCAACGAACC     1740

GGATACCCGT CCGCAAGTGC ACGGGAATAT TTCGCCACTG GCGGAAGCAA CGCGTAAACT     1800

CGACCCGACG CGTCCGATCA CCTGCGTCAA TGTAATGTTC TGCGACGCTC ACACCGATAC     1860

CATCAGCGAT CTCTTTGATG TGCTGTGCCT GAACCGTTAT TACGGATGGT ATGTCCAAAG     1920

CGGCGATTTG GAAACGGCAG AGAAGGTACT GGAAAAAGAA CTTCTGGCCT GGCAGGAGAA     1980

ACTGCATCAG CCGATTATCA TCACCGAATA CGGCGTGGAT ACGTTAGCCG GGCTGCACTC     2040

AATGTACACC GACATGTGGA GTGAAGAGTA TCAGTGTGCA TGGCTGGATA TGTATCACCG     2100

CGTCTTTGAT CGCGTCAGCG CCGTCGTCGG TGAACAGGTA TGGAATTTCG CCGATTTTGC     2160

GACCTCGCAA GGCATATTGC GCGTTGGCGG TAACAAGAAA GGGATCTTCA CTCGCGACCG     2220

CAAACCGAAG TCGGCGGCTT TTCTGCTGCA AAAACGCTGG ACTGGCATGA ACTTCGGTGA     2280

AAAACCGCAG CAGGGAGGCA AACAATGAAT CAACAACTCT CCTGGCGCAC CATCGTCGGC     2340

TACAGCCTCG GTGGGAATT NNNNGAGCTC GATCGTCAA ACATTTGGCA ATAAAGTTTC     2400

TTAAGATTGA ATCCTGTTGC CGGTCTTGCG ATGATTATCA TATAATTTCT GTTGAATTAC     2460

GTTAAGCATG TAATAATTAA CATGTAATGC ATGACGTTAT TTATGAGATG GGTTTTTATG     2520

ATTAGAGTCC CGCAATTATA CATTTAATAC GCGATAGAAA ACAAAATATA GCGCGCAAAC     2580

TAGGATAAAT TATCGCGCGC GGTGTCATCT ATGTTACTAG ATCNNNNGAA TTC            2633
```

(2) INFORMATION FOR SEQ ID NO:3:

(i) SEQUENCE CHARACTERISTICS:
        (A) LENGTH: 5534 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vii) IMMEDIATE SOURCE:
        (B) CLONE: pUMIGIT (xi) SEQUENCE DESCRIPTION: SEQ ID NO:3:

```
CNNNNCCCGG AGGACAGTAC TCCGCCCCCG GAGGACAGTA CTCCGCCCCC GGAGGACAGT      60

ACTCCGCCCC CGGAGGACAG TACTCCGCCC CCGGAGGACA GTACTCCGCC CCCGGAGGAC     120

AGTACTCCGC CCCCGGAGGA CAGTACTCCG CCCCCGGAGG ACAGTACTCC GCCCCCGGAG     180

GACAGTACTC CGCCNNNNGG ATCCNNNNCC CGGGNNNNCT GCAGACTATC CTTCGCAAGA     240

CCCTTCCTCT ATATAAGGAA GTTCATTTCA TTYGGAGAGA ACAGGATCCN NNNGGTCAGT     300

CCCTTATGTT ACGTCCTGTA GAAACCCCAA CCCGTGAAAT CAAAAAACTC GACGGCCTGT     360

GGGCATTCAG TCTGGATCGC GAAAACTGTG GAATTGATCA GCGTTGGTGG GAAAGCGCGT     420

TACAAGAAAG CCGGGCAATT GCTGTGCCAG GCAGTTTTAA CGATCAGTTC GCCGATGCAG     480

ATATTCGTAA TTATGCGGGC AACGTCTGGT ATCAGCGCGA AGTCTTTATA CCGAAAGGTT     540

GGGCAGGCCA GCGTATCGTG CTGCGTTTCG ATGCGGTCAC TCATTACGGC AAAGTGTGGG     600

TCAATAATCA GGAAGTGATG GAGCATCAGG GCGGCTATAC GCCATTTGAA GCCGATGTCA     660

CGCCGTATGT TATTGCCGGG AAAAGTGTAC GTAAGTTTCT GCTTCTACCT TGATATATA      720

TATAATAATT ATCATTAATT AGTAGTAATA TAATATTTCA AATATTTTTT TCAAAATAAA     780

AGAATGTAGT ATATAGCAAT TGCTTTTCTG TAGTTTATAA GTGTGTATAT TTTAATTTAT     840

AACTTTTCTA ATATATGACC AAAATTTGTT GATGTGCAGG TATCACCGTT TGTGTGAACA     900

ACGAACTGAA CTGGCAGACT ATCCCGCCGG GAATGGTGAT TACCGACGAA AACGGCAAGA     960

AAAAGCAGTC TTACTTCCAT GATTTCTTTA ACTATGCCGG AATCCATCGC AGCGTAATGC    1020

TCTACACCAC GCCGAACACC TGGGTGGACG ATATCACCGT GGTGACGCAT GTCGCGCAAG    1080

ACTGTAACCA CGCGTCTGTT GACTGGCAGG TGGTGGCCAA TGGTGATGTC AGCGTTGAAC    1140

TGCGTGATGC GGATCAACAG GTGGTTGCAA CTGGACAAGG CACTAGCGGG ACTTTGCAAG    1200

TGGTGAATCC GCACCTCTGG CAACCGGGTG AAGGTTATCT CTATGAACTG TGCGTCACAG    1260

CCAAAAGCCA GACAGAGTGT GATATCTACC CGCTTCGCGT CGGCATCCGG TCAGTGGCAG    1320

TGAAGGGCCA ACAGTTCCTG ATTAACCACA AACCGTTCTA CTTTACTGGC TTTGGTCGTC    1380

ATGAAGATGC GGACTTACGT GGCAAAGGAT TCGATAACGT GCTGATGGTG CACGACCACG    1440

CATTAATGGA CTGGATTGGG GCCAACTCCT ACCGTACCTC GCATTACCCT TACGCTGAAG    1500

AGATGCTCGA CTGGGCAGAT GAACATGGCA TCGTGGTGAT TGATGAAACT GCTGCTGTCG    1560

GCTTTAACCT CTCTTTAGGC ATTGGTTTCG AAGCGGGCAA CAAGCCGAAA GAACTGTACA    1620

GCGAAGAGGC AGTCAACGGG GAAACTCAGC AAGCGCACTT ACAGGCGATT AAAGAGCTGA    1680

TAGCGCGTGA CAAAAACCAC CCAAGCGTGG TGATGTGGAG TATTGCCAAC GAACCGGATA    1740
```

```
CCCGTCCGCA AGTGCACGGG AATATTTCGC CACTGGCGGA AGCAACGCGT AAACTCGACC    1800

CGACGCGTCC GATCACCTGC GTCAATGTAA TGTTCTGCGA CGCTCACACC GATACCATCA    1860

GCGATCTCTT TGATGTGCTG TGCCTGAACC GTTATTACGG ATGGTATGTC CAAAGCGGCG    1920

ATTTGGAAAC GGCAGAGAAG GTACTGGAAA AAGAACTTCT GGCCTGGCAG GAGAAACTGC    1980

ATCAGCCGAT TATCATCACC GAATACGGCG TGGATACGTT AGCCGGGCTG CACTCAATGT    2040

ACACCGACAT GTGGAGTGAA GAGTATCAGT GTGCATGGCT GGATATGTAT CACCGCGTCT    2100

TTGATCGCGT CAGCGCCGTC GTCGGTGAAC AGGTATGGAA TTTCGCCGAT TTTGCGACCT    2160

CGCAAGGCAT ATTGCGCGTT GGCGGTAACA AGAAAGGGAT CTTCACTCGC GACCGCAAAC    2220

CGAAGTCGGC GGCTTTTCTG CTGCAAAAAC GCTGGACTGG CATGAACTTC GGTGAAAAAC    2280

CGCAGCAGGG AGGCAAACAA TGAATCAACA ACTCTCCTGG CGCACCATCG TCGGCTACAG    2340

CCTCGGTGGG GAATTNNNNG AGCTCGATCG TTCAAACATT TGGCAATAAA GTTTCTTAAG    2400

ATTGAATCCT GTTGCCGGTC TTGCGATGAT TATCATATAA TTTCTGTTGA ATTACGTTAA    2460

GCATGTAATA ATTAACATGT AATGCATGAC GTTATTTATG AGATGGGTTT TTATGATTAG    2520

AGTCCCGCAA TTATACATTT AATACGCGAT AGAAAACAAA ATATAGCGCG CAAACTAGGA    2580

TAAATTATCG CGCGCGGTGT CATCTATGTT ACTAGATCNN NNGAATTCGA TATCAAGCTT    2640

ATCGATACCG TCGACCTCGA GGGGGGGCCC GGTACCCAAT TCGCCCTATA GTGAGTCGTA    2700

TTACGCGCGC TCACTGGCCG TCGTTTTACA ACGTCGTGAC TGGGAAAACC CTGGCGTTAC    2760

CCAACTTAAT CGCCTTGCAG CACATCCCCC TTTCGCCAGC TGGCGTAATA GCGAAGAGGC    2820

CCGCACCGAT CGCCCTTCCC AACAGTTGCG CAGCCTGAAT GGCGAATGGG ACGCGCCCTG    2880

TAGCGGCGCA TTAAGCGCGG CGGGTGTGGT GGTTACGCGC AGCGTGACCG CTACACTTGC    2940

CAGCGCCCTA GCGCCCGCTC CTTTCGCTTT CTTCCCTTCC TTTCTCGCCA CGTTCGCCGG    3000

CTTTCCCCGT CAAGCTCTAA ATCGGGGGCT CCCTTTAGGG TTCCGATTTA GTGCTTTACG    3060

GCACCTCGAC CCCAAAAAAC TTGATTAGGG TGATGGTTCA CGTAGTGGGC CATCGCCCTG    3120

ATAGACGGTT TTTCGCCCTT TGACGTTGGA GTCCACGTTC TTTAATAGTG GACTCTTGTT    3180

CCAAACTGGA ACAACACTCA ACCCTATCTC GGTCTATTCT TTTGATTTAT AAGGGATTTT    3240

GCCGATTTCG GCCTATTGGT TAAAAAATGA GCTGATTTAA CAAAAATTTA ACGCGAATTT    3300

TAACAAAATA TTAACGCTTA CAATTTAGGT GGCACTTTTC GGGGAAATGT GCGCGGAACC    3360

CCTATTTGTT TATTTTTCTA AATACATTCA AATATGTATC CGCTCATGAG ACAATAACCC    3420

TGATAAATGC TTCAATAATA TTGAAAAAGG AAGAGTATGA GTATTCAACA TTTCCGTGTC    3480

GCCCTTATTC CCTTTTTTGC GGCATTTTGC CTTCCTGTTT TTGCTCACCC AGAAACGCTG    3540

GTGAAAGTAA AAGATGCTGA AGATCAGTTG GGTGCACGAG TGGGTTACAT CGAACTGGAT    3600

CTCAACAGCG GTAAGATCCT TGAGAGTTTT CGCCCCGAAG AACGTTTTCC AATGATGAGC    3660

ACTTTTAAAG TTCTGCTATG TGGCGCGGTA TTATCCCGTA TTGACGCCGG GCAAGAGCAA    3720

CTCGGTCGCC GCATACACTA TTCTCAGAAT GACTTGGTTG AGTACTCACC AGTCACAGAA    3780

AAGCATCTTA CGGATGGCAT GACAGTAAGA GAATTATGCA GTGCTGCCAT AACCATGAGT    3840

GATAACACTG CGGCCAACTT ACTTCTGACA ACGATCGGAG GACCGAAGGA GCTAACCGCT    3900

TTTTTGCACA ACATGGGGGA TCATGTAACT CGCCTTGATC GTTGGGAACC GGAGCTGAAT    3960

GAAGCCATAC CAAACGACGA GCGTGACACC ACGATGCCTG TAGCAATGGC AACAACGTTG    4020

CGCAAACTAT TAACTGGCGA ACTACTTACT CTAGCTTCCC GGCAACAATT AATAGACTGG    4080

ATGGAGGCGG ATAAAGTTGC AGGACCACTT CTGCGCTCGG CCCTTCCGGC TGGCTGGTTT    4140
```

```
ATTGCTGATA AATCTGGAGC CGGTGAGCGT GGGTCTCGCG GTATCATTGC AGCACTGGGG    4200

CCAGATGGTA AGCCCTCCCG TATCGTAGTT ATCTACACGA CGGGGAGTCA GGCAACTATG    4260

GATGAACGAA ATAGACAGAT CGCTGAGATA GGTGCCTCAC TGATTAAGCA TTGGTAACTG    4320

TCAGACCAAG TTTACTCATA TATACTTTAG ATTGATTTAA AACTTCATTT TTAATTTAAA    4380

AGGATCTAGG TGAAGATCCT TTTTGATAAT CTCATGACCA AAATCCCTTA ACGTGAGTTT    4440

TCGTTCCACT GAGCGTCAGA CCCCGTAGAA AAGATCAAAG GATCTTCTTG AGATCCTTTT    4500

TTTCTGCGCG TAATCTGCTG CTTGCAAACA AAAAAACCAC CGCTACCAGC GGTGGTTTGT    4560

TTGCCGGATC AAGAGCTACC AACTCTTTTT CCGAAGGTAA CTGGCTTCAG CAGAGCGCAG    4620

ATACCAAATA CTGTCCTTCT AGTGTAGCCG TAGTTAGGCC ACCACTTCAA GAACTCTGTA    4680

GCACCGCCTA CATACCTCGC TCTGCTAATC CTGTTACCAG TGGCTGCTGC CAGTGGCGAT    4740

AAGTCGTGTC TTACCGGGTT GGACTCAAGA CGATAGTTAC CGGATAAGGC GCAGCGGTCG    4800

GGCTGAACGG GGGGTTCGTG CACACAGCCC AGCTTGGAGC GAACGACCTA CACCGAACTG    4860

AGATACCTAC AGCGTGAGCT ATGAGAAAGC GCCACGCTTC CCGAAGGGAG AAAGGCGGAC    4920

AGGTATCCGG TAAGCGGCAG GGTCGGAACA GGAGAGCGCA CGAGGGAGCT TCCAGGGGGA    4980

AACGCCTGGT ATCTTTATAG TCCTGTCGGG TTTCGCCACC TCTGACTTGA GCGTCGATTT    5040

TTGTGATGCT CGTCAGGGGG GCGGAGCCTA TGGAAAAACG CCAGCAACGC GGCCTTTTTA    5100

CGGTTCCTGG CCTTTTGCTG GCCTTTTGCT CACATGTTCT TTCCTGCGTT ATCCCCTGAT    5160

TCTGTGGATA ACCGTATTAC CGCCTTTGAG TGAGCTGATA CCGCTCGCCG CAGCCGAACG    5220

ACCGAGCGCA GCGAGTCAGT GAGCGAGGAA GCGGAAGAGC GCCCAATACG CAAACCGCCT    5280

CTCCCCGCGC GTTGGCCGAT TCATTAATGC AGCTGGCACG ACAGGTTTCC CGACTGGAAA    5340

GCGGGCAGTG AGCGCAACGC AATTAATGTG AGTTAGCTCA CTCATTAGGC ACCCCAGGCT    5400

TTACACTTTA TGCTTCCGGC TCGTATGTTG TGTGGAATTG TGAGCGGATA ACAATTTCAC    5460

ACAGGAAACA GCTATGACCA TGATTACGCC AAGCGCGCAA TTAACCCTCA CTAAAGGGAA    5520

CAAAAGCTGG AGCT                                                     5534
```

(2) INFORMATION FOR SEQ ID NO:4:

(i) SEQUENCE CHARACTERISTICS:
        (A) LENGTH: 793 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

```
GCTCTAGAAA CAATGCGAAG CTCGGCTAAG CAAGAAGAAC TAGTTAAAGC ATTTAAAGCA      60

TTACTTAAAG AAGAGAAATT TAGCTCCCAG GGCGAAATCG TCGCCGCGTT GCAGGAGCAA     120

GGCTTTGACA ATATTAATCA GTCTAAAGTC TCGCGGATGT TGACCAAGTT TGGTGCTGTA     180

CGTACACGCA ATGCCAAAAT GGAAATGGTT TACTGCCTGC CAGCTGAACT GGGTGTACCA     240

ACCACCTCCA GTCCATTGAA GAATCTGGTC CTGGATATCG ACTACAACGA TGCAGTTGTC     300

GAATTCGCCA ATTTTAATCA AAGTGGGAAT ATTGCTGATA GCTCATTGTC CTTCACTTTC     360

ACTACAGTAG CAACGGTCCG AACCTCATAA CAACTCAAAC AAATTCTCAA GCGCTTTCAC     420
```

```
AACCAATTGC CTCCTCTAAC GTTCATGATA ACTTCATGAA TAATGAAATC ACGGCTAGTA      480

AAATTGATGA TGGTAATAAT TCAAAACCAC TGCACCTGGT TGGACGGACC AAACTGCGTA      540

TACGCGTTTG GAATCACTAC GGATGTTTAA TACCACTACA ATGGATGATG TATATAACTA      600

TCTATTCGTG ATGAAGATAC CCCACCAAAC CCAAAAAAAG AGTAAAATGA ATCGTAGATA      660

CTGAAAAACC CCGCAAGTTC ACTTCAACTG TGCATCGTGC ACCATCTAAT TTCTTTCATT      720

TATACATCGT TTTGCCTTCT TTTATGTAAC TATACTCCTC TAAGTTTCAA TCTTGGCCAT      780

GTAACCTCTG ATC                                                        793
```

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

```
GCTCTAGAAA CAATGCGAAG CTCGGCTAAG                                       30
```

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

```
GGAATTCGAC AACTGCATCG TTGTA                                            25
```

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

```
GCTCTAGAAT TGTGAAATGG GGT                                              23
```

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: double -continued

```
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

GCCTGCAGCG CATGGCGAAC GCCACT                                            26

(2) INFORMATION FOR SEQ ID NO:9:

(i) SEQUENCE CHARACTERISTICS:
         (A) LENGTH: 93 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

GCTCTAGAAT TGTGAAATGG GGTTGCAAAT GAATAATTAC ACATATAAAG TGAATTTTAA        60

TTCAATAAGT GGCGTTCGCC ATGCGCTGCA GGC                                    93
```

METHOD OF USING TRANSACTIVATION PROTEINS TO CONTROL EXPRESSION IN TRANSGENIC PLANTS

CROSS-REFERENCE TO RELATED APPLICATIONS

This is a Continuation in Part of U.S. application Ser. No. 08/452,267 filed May 26, 1995, now U.S. Pat. No. 5,801,027, which claims priority under 35 U.S.C. §119 to Great Britain application serial No. 9502456.8, filed Feb. 8, 1995.

FIELD OF THE INVENTION

The current application relates to the control of transgenes in plants by the use of a transactivating protein.

BACKGROUND AND SUMMARY OF THE INVENTION

The commercial exploitation of plants using genetic engineering has been an industrial goal for over a decade. Conventional approaches to the regulation of plant transgene expression by the fusing of a highly expressed promoter element directly with the gene coding sequence has proved insufficient to meet the stringent safety and technical demands of plant biotechnology today. Environmentally there is a serious risk of genetically releasing an actively expressed trait, such as herbicide resistance, into plant populations. Commercially the exploitation of plants by transgenic modification, as described for example by Koning et al (Plant Mol. Biol. Vol 18, pages 247–258 (1992)), such as through the introduction of a novel biochemical pathway such as polyhydroxybutyrate synthesis (described in WO92/19747 (ICI)) is hampered by the inability to introduce and coordinately regulate multiple transgenes in transgenic crops. The conventional approach would involve fusing each biosynthetic gene to a common promoter element, followed by their repeated transformation into a transgenic plant, as described for example in WO92/19747 (ICI). Practically, this approach is time-consuming, limits further alterations of transgene expression and rather than enabling coordinate transgene expression can lead to cosuppression of other transgenes, Meyer P. and Saedler H, Ann. Rev. Plant Physiol. Plant. Mol. Biol., 1996, vol. 47, pages 23–48, and Baulcombe D. C. and English J. J., Curr. Opin. Biotech., 1996, vol. 7, pages 173–180).

The present invention is directed to a novel approach to the control of transgenes in plants. Instead of using the regulatory and expressed sequences in conventional cis fashion, the present invention rearranges the regulatory and expressed sequences so that they are used in a trans fashion.

The promoter element now indirectly regulates the transgene(s) via a transcriptional activating protein intermediate. The immediate outcome of this is that two plant lines can be produced; one which contains transgene(s) encoding for a desired phenotype and one which contains a transgene encoding for the regulatory transactivating protein. This means that the desired phenotypic trait is only fully expressed once both of the sets of transgenes have come together in an F1 hybrid plant. The regulatory and phenotype transgenes will then segregate apart in subsequent generations.

This has major safety implications because it means that the chances of an active transgene encoding for a phenotypic trait, such as herbicide resistance, being released into the environment is considerably reduced. Safety can be further enhanced by making one of the plants containing the transgenes male sterile, so that pollen contain the transgene is not released. This also has advantages for seed companies marketing high value genetically engineered traits because, if a farmer attempts to use F2 generation seed, he will see a dramatic reduction in the amount of product produced by the F2 generation plants.

The use of a transcriptional protein also has the added advantage that several transgenes can be controlled by the same transactivating protein, without the problems of cosuppression seen with conventional cis acting systems.

By physically separating the promoter regulatory and target sequences within independent transgenic plants, different transgene expression can be selected for in the F1 generation simply by crossing the transgenic target line with regulator lines that express the transactivating protein in particular spatial and temporal patterns (e.g. seed or leaf). Hence, this system allows the rapid introduction and fine-tuning of commercially attractive single or multiple gene traits in transgenic crops.

It also allows a useful tissue specific, but weakly expressed promoter to be used, since the transactivating protein works in low concentrations.

The preferred transactivating protein used is GAL4 from the yeast, *Saccharomyces cerevisiae* or ArgR from *E-coli*.

The expression of genes encoding enzymes of the galactose and melibiose metabolic pathways in the yeast *Saccharomyces cerevisiae* is stringently regulated by the available carbon source (Johnston, Microbiol. Rev., Vol. 51, pages 458–476 (1987)). Transcriptional control is mediated through the positive regulatory protein GAL4 and the negative regulatory protein GAL80. In the presence of galactose GAL4 divergently promotes transcription of the genes of the galactose regulon. Transcriptional activation by GAL4 results in a 1,000 fold increase in the level of gene expression. When the inducer is absent GAL80 inhibits the transactivating ability of GAL4. A number of additional transcriptional control mechanisms operate in the presence of glucose. These mechanisms, collectively termed catabolite repression, ensure that glucose is the preferred carbon source.

Native GAL4 is 881 amino acid (aa) residues in length and has a molecular weight of 99,000. Deletion and domain swap analyses have demonstrated that GAL4 is comprised of a number of functionally delineated domains, the combined activities of which account for the protein's in vivo characteristics (Ma & Ptashne, Cell. Vol. 48, pages 847–853, (1987); Brent & Ptashne, Cell. Vol. 43, pages 729–736, (1985). GAL4 binds to a 17 base-pair (bp) sequence exhibiting dyad symmetry, termed the galactose upstream activating sequence ($UAS_G$). In the presence of galactose GAL4 activates expression of genes linked to the $UAS_G$ (West et al., Mol. Cell. Biol., Vol. 4, pages 2467–2478) (1984). A consensus sequence of the naturally occurring site will also mediate GAL4 stimulatory action (Giniger et al., Cell, Vol. 40, pages 767–774, (1985); Lord et al., J. Mol. Biol., Vol. 186, pages 821–824 (1985). The amino terminal (N-terminal) 65 aa residues of GAL4 are responsible for sequence specific-binding (Keegan et al., Sci. Vol. 231, pages 699–704 (1986); Johnston, Nature, Vol. 328, pages 353–355 (1987). Sequence-specific binding is absolutely dependent on the presence of a divalent cation coordinated by the 6 cysteine residues present in the DNA binding domain. The zinc-containing domain recognizes a conserved CCG triplet at the end of each 17 bp site via direct contacts with the major groove (Marmorstein et al., Nature. Vol. 356, pages 408–414 (1992). Each target DNA sequence binds GAL4 as a dimer (Carey et al., J. Mol. Biol. Vol. 209, pages 423–432 (1989), a function ascribed to aa residues 65–94. Also present in the N-terminal 1–78 aa residues is a nuclear localization sequence (Silver et al, PNAS (USA), Vol. 81, pages 5951–5955 (1984).

Binding of GAL4 to its target DNA sequence is insufficient to direct RNA polymerase II dependent transcription of linked genes. The DNA binding function of the protein serves solely to position the carboxy-terminal (C-terminal) transcriptional activating domains in the vicinity of the promoter. Transcriptional activation is conferred by 2 major activating domains termed activating region I (ARI-aa residues 148–196) and activating region II (ARII-aa residues 767–881), of which ARII is the more potent (Ma & Ptashne, Supra). A third cryptic transactivating region (aa residues 75–147) has been identified in GAL4 deletion derivatives and exhibits in vitro activity (Lin et al., Cell. Vol. 54, pages 659–664 (1988). Each of the three transcriptional activation domains is characterized by a high proportion of negatively charged aa residues and hence are known as acidic activation domains (AAD). In the absence of a DNA-binding domain the activating regions are unable to function.

The mechanisms responsible for eukaryotic transcriptional activation have been evolutionary conserved. This is indicated by the fact that the yeast transcriptional activator GAL4 can activate gene expression in other eukaryotic organisms. Native GAL4 has been demonstrated to activate transcription of genes linked to the GAL4 binding site (either synthetic or the UASG) in insect (Fischer et al. (1987) and mammalian cells (Kakidani & Ptashne, Cell. Vol. 52, pages 161–167 (1988); Webster et al., Cell. Vol. 52, pages 169–178 (1988). Full length GAL4 is, however, incapable of stimulating transcription in plant protoplasts possibly as a result of its inefficient synthesis or instability (Ma et al., Nature, Vol. 334, pages 631–633 (1988). Deletion derivatives of GAL4 are able to activate transcription in yeast. These proteins, comprised of aa residues 1–147 (DNA-binding domain) and ART and/or ARII also exhibit activity in mammalian cells (Kakidani & Ptashne, Supra) and plant protoplasts (Ma et al., Supra).

ArgR is the arginine repressor from *Escherichia coil*. The action and isolation of ArgR is reviewed in the article by Werner K Maas (Micorbiol. Reviews, 1994, Vol. 58 (4), pages 631–640), incorporated herein by reference.

The product of the ArgR gene, in conjunction with L-arginine, controls the synthesis of the 10 enzymes of arginine biosynthesis and also its own synthesis. The ArgR gene product in its native form acts as a repressor of transcription. The 12 genes of the arginine regulon are organized into nine transcriptional units, each containing an operator site overlapping a promotor. An operator site consists of two 18-bp palindromic sequences referred to as ARG boxes to which the repressor binds.

The inventors realized that, whilst ArgR in its native state is a repressor, the ArgR DNA binding domain may be used to form chimera constructs with parts of other genes such as, for example the GAL 4 activation domain II, which may be used as transgene activators.

Two recent reports have demonstrated transgene expression of a target gene arranged in trans with a control gene in Drosophila (Brand & Perrimon, Development, Vol. 118, pages 401–415 (1993) and Crieg & Akam, Nature, Vol. 362, pages 630–632 (1993)). Neither of these discuss the possibility of using such a system in plants.

The system described herein can be used to control the production of products or of a desired trait such as herbicide resistance. A preferred multigene system is the use of genes involved in the biosynthesis of polyhydroxybutyrate (PHB), controlled by a transactivating protein.

PHB is a commercially important biodegradable polymer which has previously been produced in plants using conventional cis acting control, as described in WO92/19747 (ICI) and Pimer et al (Science, Vol 256, pages 529–523 (1992)). It is, however, an ideal product to be produced by the invention since the multigene pathway is subject to the problems of cosuppression when used in conventional systems and the trans regulating system described herein enables the PHB to be produced more safely than existing methods of producing its implants.

Other genes which may be controlled include genes for controlling male sterility, such as the ribonuclease barnase and its inhibitory subunit barstar (Mariani C. et al, Nature, 1990. vol. 347, pages 737–741). Antisense or sense RNA mediated inhibition of target mRNAs such as polygalactonuronidase and ACC oxidase during tomato ripening may also be controlled by the transgene system of the invention (Smith C. J. et al. Nature, 1988, vol. 334, pages 724–726 and Hamilton A. J. et al. Nature, 1990, vol. 346, pages 284–287).

It is therefore an object of the invention to produce an inherently safe method of producing a phenotypic trait in transgenic plants.

It is another object to produce a method of regulating two or more genes in a plant without the problems of cosuppression of the genes associated with conventional methods.

DETAILED DESCRIPTION OF THE PREFERRED EMBODIMENTS

Figure 1A:
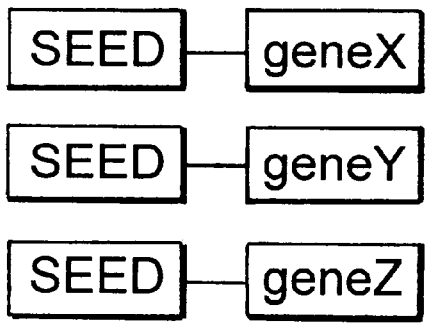
FIG. 1a is a diagrammatic representation of the conventional method of regulating gene expression using cis acting control elements.

A first aspect of the invention provides a method of producing a plant exhibiting one or more desired phenotypic traits, said method comprising the steps of:

fertilizing a first transgenic plant with genetic material from a second transgenic plant to produce reproductive material, wherein:

one of the plants comprises at least one nucleic acid sequence encoding a desired phenotypic trait operatively linked to an upstream activating sequence (UAS) recognition site; and the other plant comprises nucleic acid encoding a promoter operatively linked to a nucleic acid sequence encoding a transactivating protein which is capable of activating said UAS sequence; and growing the reproductive material into a plant exhibiting the desired phenotypic trait.

A second aspect of the invention provides a method of producing plant reproductive material, said method comprising the steps of:

fertilizing a first transgenic plant with genetic material from a second transgenic plant to produce the plant reproductive material, wherein:

one of the plants comprises at least one nucleic acid sequence encoding a desired phenotypic trait operatively linked to an upstream activating sequence (UAS) recognition site; and the other plant comprises nucleic acid encoding a promoter operatively linked to a nucleic acid sequence encoding a transactivating protein which is capable of activating said UAS sequence.

Preferably the first transgenic plant is pollinated from the second transgenic plant and the reproductive material may be seed. Preferably the first transgenic plant is male sterile.

The phenotypic trait may, for example, be the production of a product or herbicide resistance.

In accordance with one embodiment a method for producing a plant exhibiting one or more desired phenotypic traits is described. The method comprises the steps of providing a first and second plant and pollinating the first plant with pollen from the second plant, wherein one of the plants comprises a nucleic acid sequence encoding for herbicide resistance, operatively linked to an upstream activating sequence that is activated by a transactivation protein (such as GAL4), and the other plant comprises a nucleic acid sequence encoding for the transactivating protein (such as GAL4, or a derivative thereof).

A third aspect of the invention provides a method of controlling two or more genes in a plant comprising the steps of inserting into a plant;

two or more exogenous genes, each of which is operatively linked to a nucleic acid sequence encoding for a heterologous upstream activating sequence (UAS) recognition site; and nucleic acid encoding for a promoter operatively linked to a nucleic acid sequence encoding for a transactivating protein which is capable of activating the UAS sequence. In one embodiment, one of the plants comprises nucleic acid sequences encoding for the production of a polyhydroxyalkanoate, wherein the nucleic acid sequences are operatively linked to an upstream activating sequence that is activated by a transactivation protein (such as GAL4), and the other plant comprises a nucleic acid sequence encoding for the transactivation protein (such GAL4, or a derivative thereof).

Preferably the transactivating protein used in the invention is GAL4 protein or a derivative thereof, preferably as encoded by or homologous with, the vector pGAL4 or comprises the ArgR DNA binding domain or a derivative thereof The UAS recognition site may be a site recognized by such proteins if they are used. Preferred UAS sequences or those used in plasmids pUMIGIT and ArgF-GUS Bsc.

The plant used may be a plant in which transgenic DNA has been inserted, such as a soft fruit, tobacco, potato, barley, rice, legume, wheat, Brassica or Arabidopsis. The selection of the plant may be dependent on a number of factors such as the ease of growing the plant and the desired phenotypic trait.

In a preferred embodiment the phenotypic trait is the production of polyhydroxyalkanoates (PHA) such as polyhydroxybutyrate (PHB). The preferred genes controlled by UAS sequences are β-ketothiolase, NADP linked acetoacetyl CoA reductase and polyhydroxybutyrate synthase, as disclosed in WO92/19747, the disclosure of which is expressly incorporated herein.

PHB production requires large amounts of acetylcoenzyme A (acetyl CoA). Oil-producing plants such a Canola, Soya, Sunflower and most preferably Oilseed Rape (*Brassica napus*) may be used to produce PHB because oil production involves the production of large amounts of acetyl CoA.

In one preferred embodiment a male sterility system is used wherein male sterility is induced through the use of genes that encode for the ribonuclease barnase and its inhibitory subunit barstar.

In accordance with one embodiment the transactivated gene or genes ecode for a protein, RNA or antisense mRNA to block or delay the onset of a phenotypic trait. In one embodiment the antisense and sense RNA inhibition genes encode for polygalactonuronidase and ACC oxidase.

The promoters used may be tissue specific to enable the desired phenotype to be specifically expressed, for example in seeds, leaves or roots. Alternatively, the promoter used may be developmentally regulated to enable the desired phenotype to be expressed during a specific developmental stage, for example during embryo development.

Preferred promoters for use in the invention are CaMV35S constitutive promoter, the promoter of the rape seed storage protein, napin, cruciferin, and promoters for fatty acid synthesis such as rape acyl carrier protein (ACP) or β-ketoacyl ACP reductase. Plants and parts of plants produced directly by the methods of the invention or from the seeds or their progeny, including seed, are also included within the scope of the invention. The invention also provides products produced by the methods of the invention.

The gene constructs used in the invention may be produced and inserted into plants using conventional methods such as the use of Agrobacterium infection methods or particle infiltration methods known in the art.

Bechtold et al (C. R. Acad. Sci., Paris Sciences de la view/Life Sciences, Vol. 316, pages 1194–9 (1993)), for example, discloses a vacuum infiltration method for infiltrating a suspension of Agrobacterium cells containing a binary T-DNA vector into Arabidopsis plants.

An alternative method, especially suitable for Brassica tissue transformation, uses young inflorescences which are sterilized and cut into segments. The segments are inverted and infected with A. *rhizogenes* containing T-DNA vectors with the transgenes of interest and cultured. The hairy roots produced are selected for transformants and multiplied in subculture. Root and leaves are induced to produce plants, and the plants are then backcrossed with wild type plants to allow gene segregation. The resulting progeny are then selected for a marker, such as NAM inhibition by NAA or Kanamycin resistance. The presence of a particular transgene can then be confirmed by PCR.

The invention will now be described with reference to the following Figures, in which:

FIG. 1a is a diagrammatic representation of the conventional method of regulating gene expression using cis acting control elements. FIG. 1a shows a multigene system in which each gene x, y and z is controlled by a separate seed promoter ("seed").

Figure 1B:
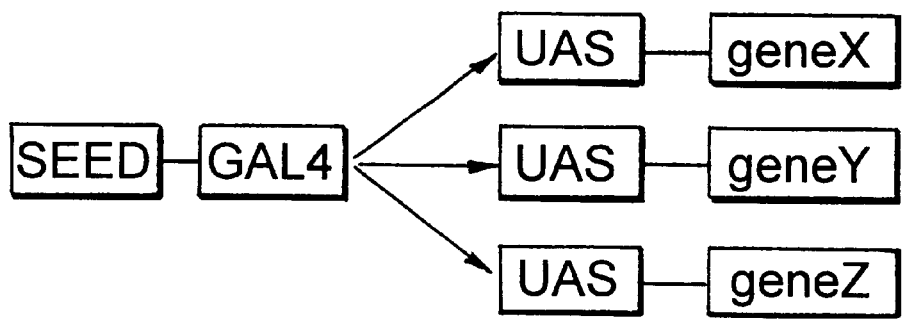
FIG. 1b is a diagrammatic representation of the regulatory mechanism utilized in the present invention, wherein the expression of multiple genes is regulated by a transactivating protein (i.e. GAL4).

FIG. 1b is a diagrammatic representation of the regulatory mechanism utilized in the present invention, wherein the expression of multiple genes is regulated by a transactivating protein (i.e. GAL4). FIG. 1b shows a seed promoter controlling the production of the GAL4 transactivating protein, which in turn activates a UAS sequence attached to each gene.

Figure 2:
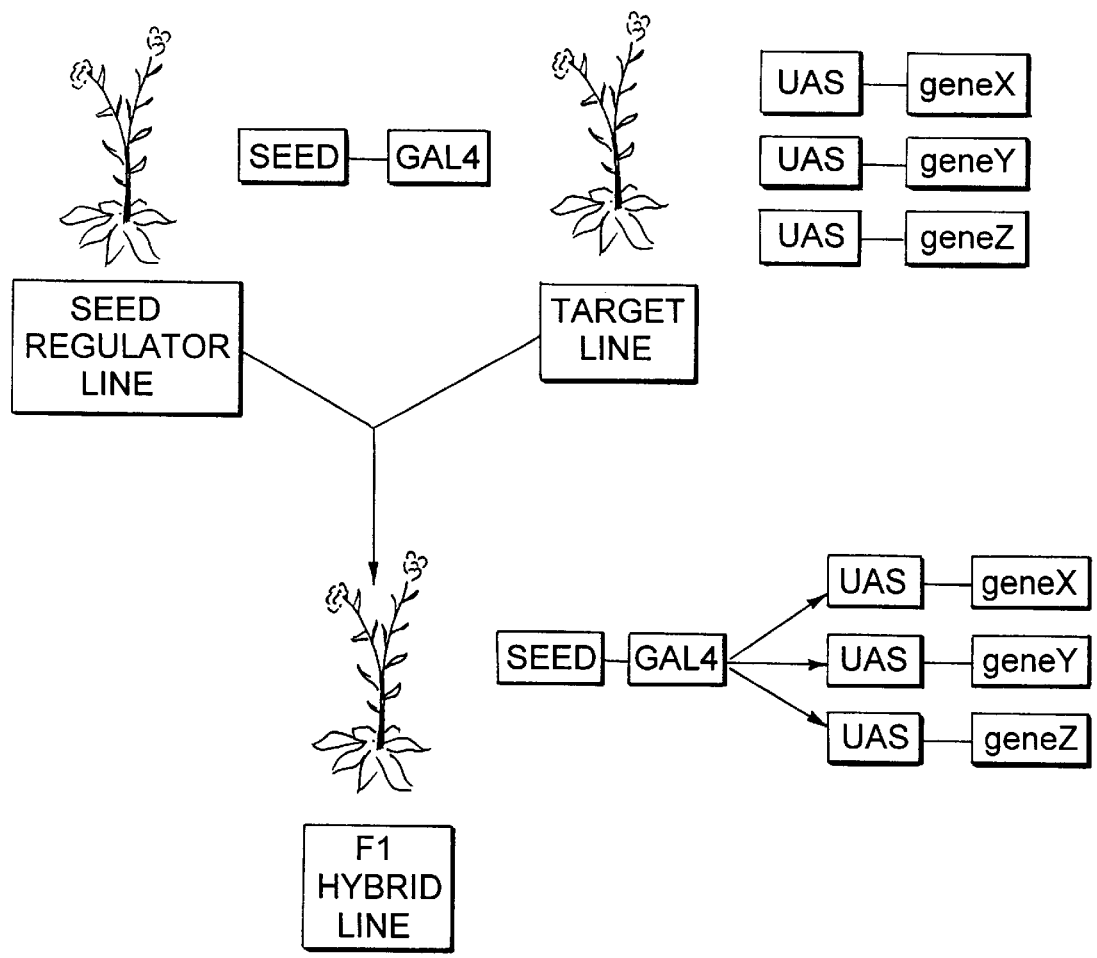
FIG. 2 is a schematic representation of the cross fertilization of a seed regulator plant line (which expresses the transactivating protein) with a target cell line (having multiple gene under the control of an upstream activating sequence, UAS) to produce an F1 hybrid that expresses the X, Y and Z gene products.

FIG. 2 is a schematic representation of the cross fertilization of a seed regulator plant line (which expresses the transactivating protein) with a target cell line (having multiple gene under the control of an upstream activating sequence, UAS) to produce an F1 hybrid that expresses the X, Y and Z gene products.

Figure 3A:
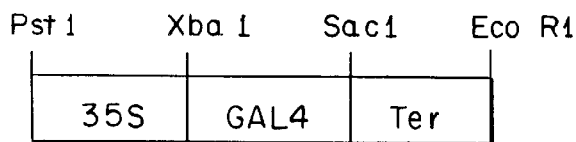
FIG. 3a is a schematic representation of one plasmid vector construct (pGAL4) suitable for use in the present invention.

FIG. 3a is a schematic representation of one plasmid vector construct (pGAL4) suitable for use in the present invention.

Figure 3B:
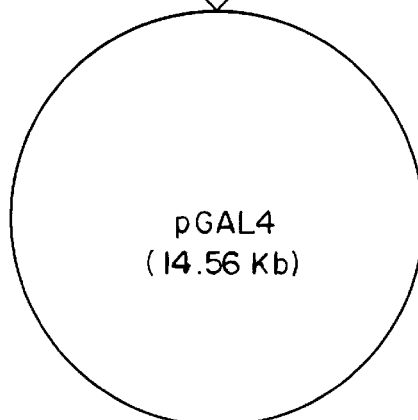
FIG. 3b is a schematic representation of the GAL4 insert, including the DNA binding site and region II activator sequences.
Figure 3B:
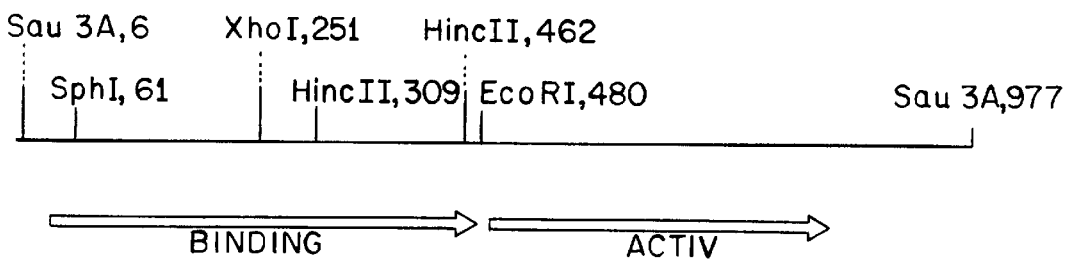

FIG. 3b is a schematic representation of the GAL4 insert, including the DNA binding site and region II activator sequences. SEQ ID NO: 1 represents the sequence of the GAL4 insert.

Figure 4:
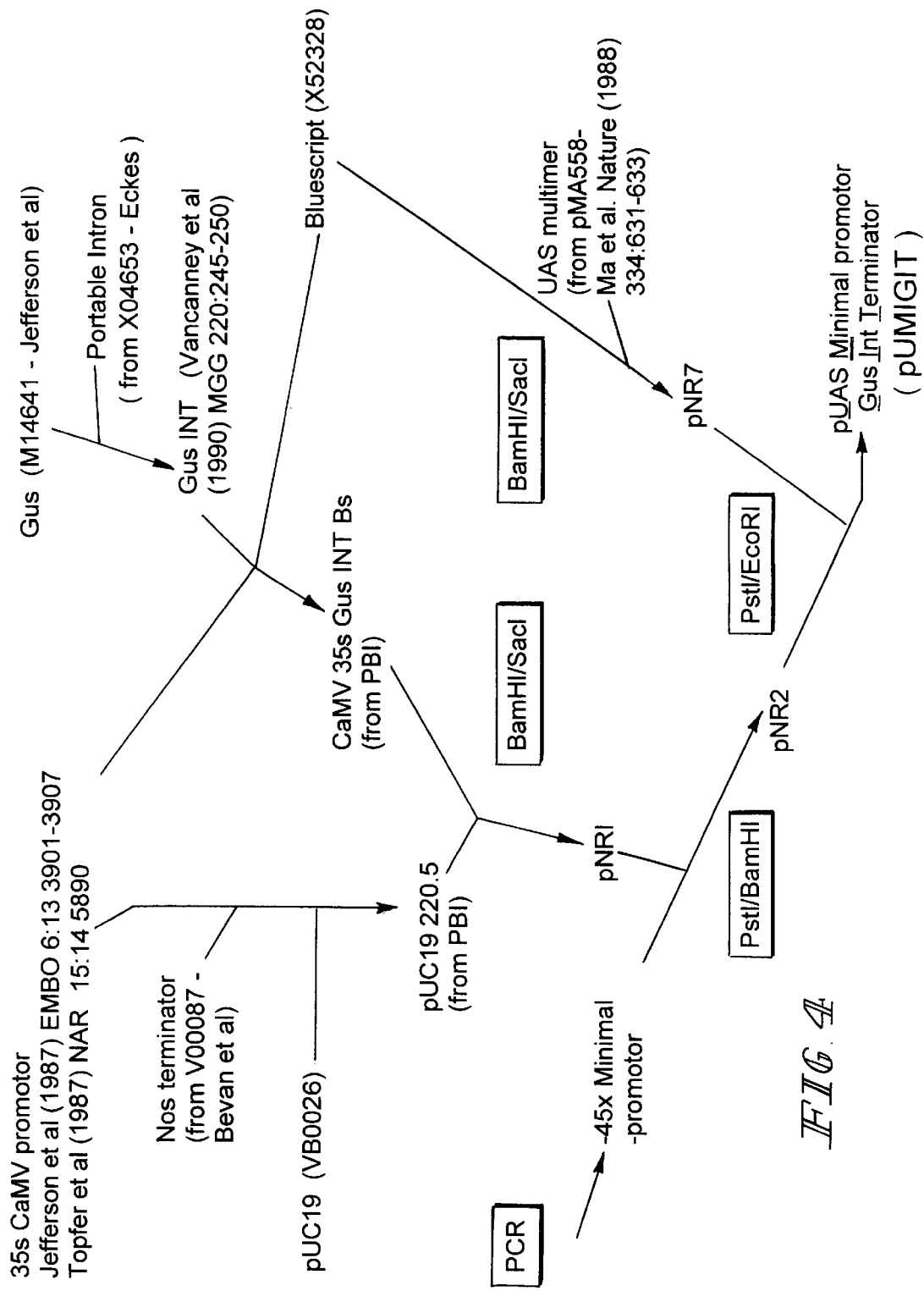
FIG. 4 is a diagrammatic representation of the strategy utilized to prepare the reporter plasmids used in the present invention.

FIG. 4 is a diagrammatic representation of the strategy utilized to prepare the reporter plasmids used in the present invention.

Figure 5A:
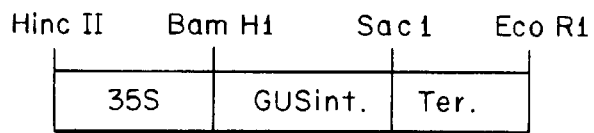
FIG. 5a is a schematic representation of plasmid construct pNR1.

FIG. 5a is a schematic representation of plasmid construct pNR1.

Figure 5B:
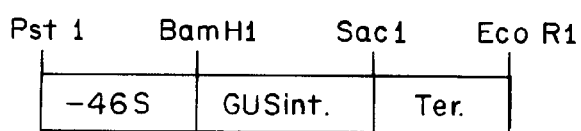
FIG. 5b is a schematic representation of plasmid construct pNR2.

FIG. 5b is a schematic representation of plasmid construct pNR2.

Figure 5C:
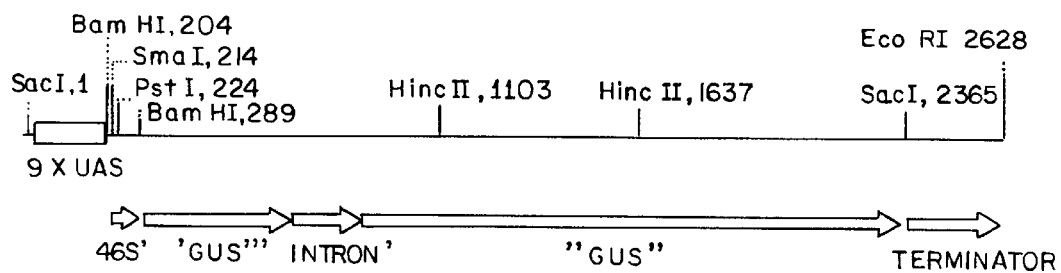
FIG. 5c is a schematic representation of the PUMIGIT insert which includes the reporter gene, GUSint, the 46S cauliflower mosaic virus promoter (CaMV) minimal promoter and the GAL4 binding sites (UAS).

FIG. 5c is a schematic representation of the pUMIGIT insert which includes the reporter gene, GUSint, the 46S cauliflower mosaic virus promoter (CaMV) minimal promoter and the GAL4 binding sites (UAS).

Figure 5D:
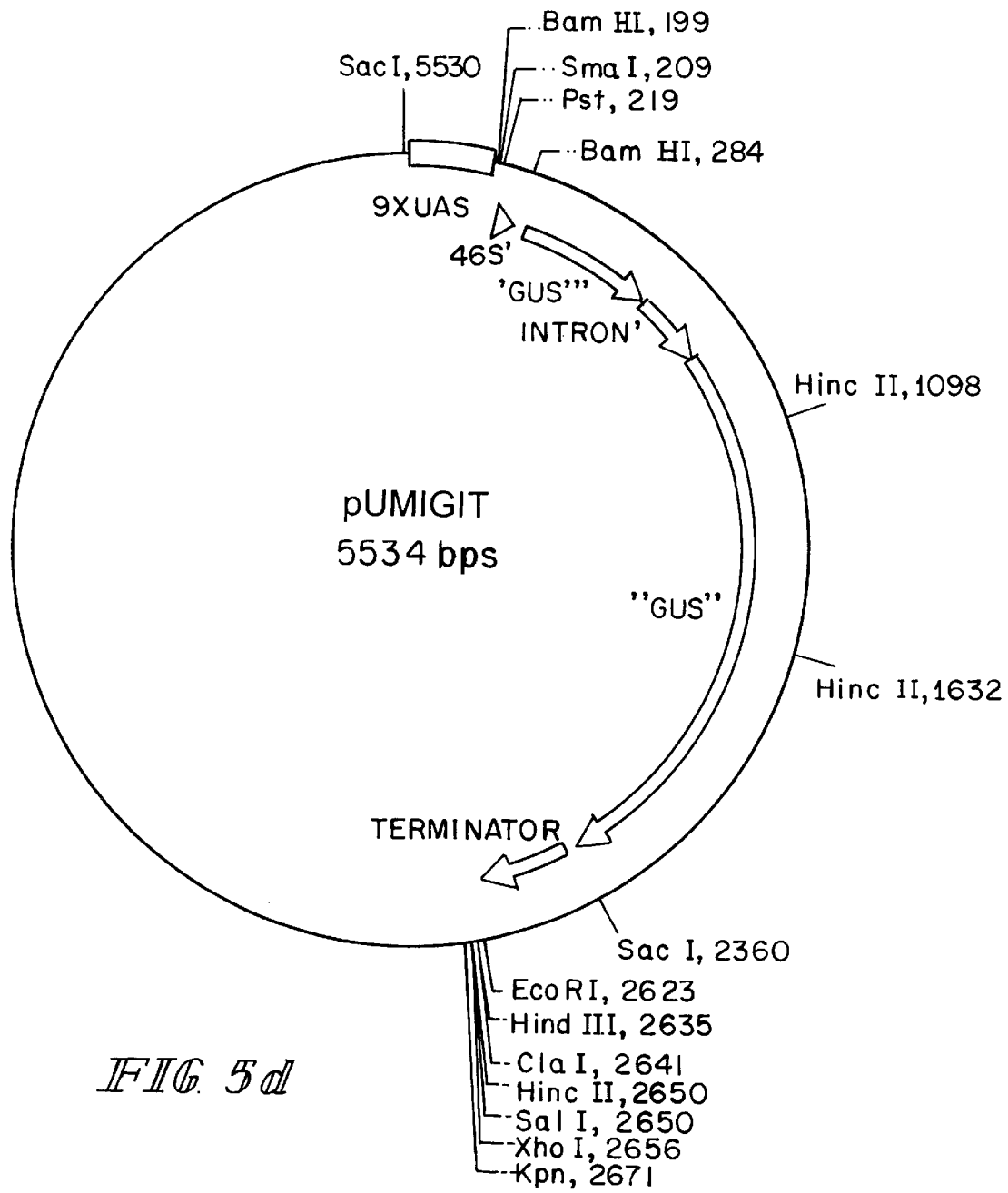
FIG. 5d is a schematic representation of plasmid construct pUMIGIT.

FIG. 5d is a schematic representation of plasmid construct pUMIGIT.

Figure 5E:
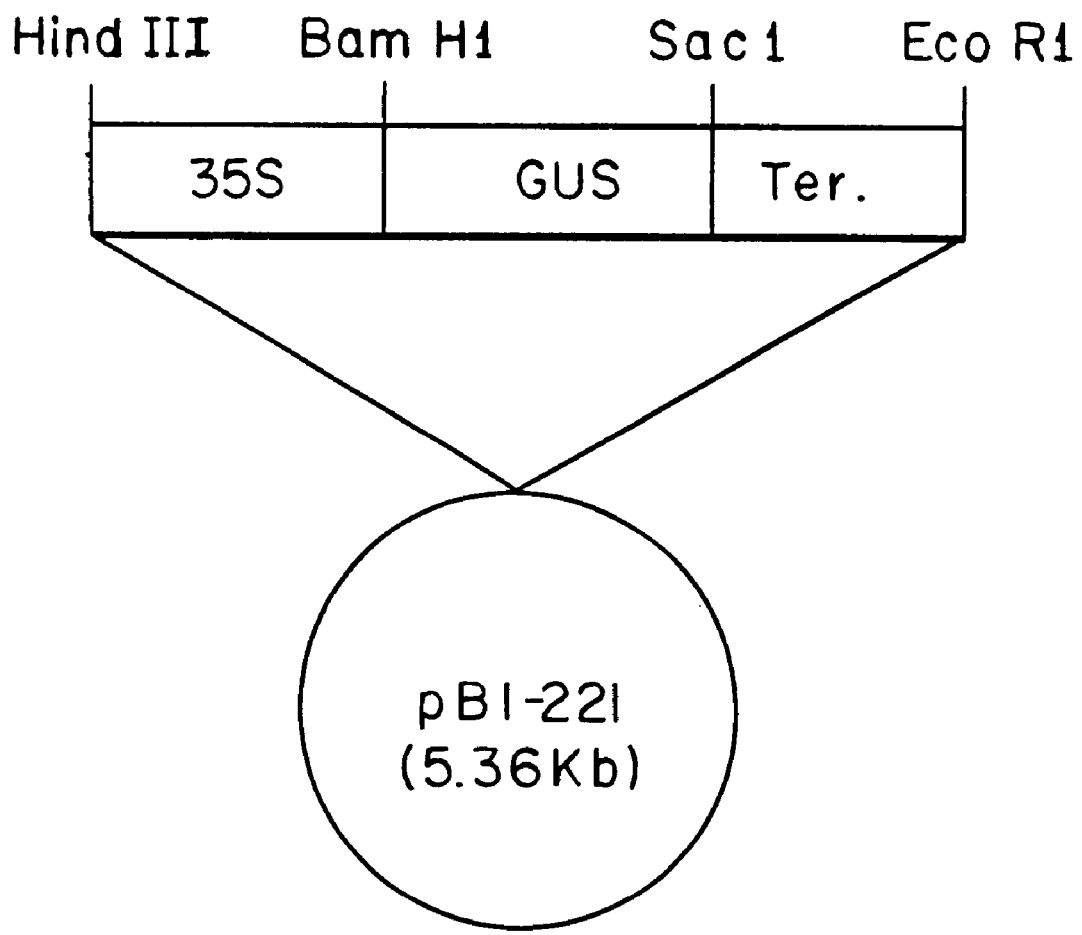
FIG. 5e is the DNA sequence of the entire pUMIGIT plasmid.

FIG. 5e is a schematic representation of plasmid construct pBI-221, wherein SEQ ID NO: 2 represents the DNA sequence of the pUMIGIT insert sequence and SEQ ID NO: 3 represents the complete sequence of the whole pUMIGIT plasmid.

Figure 6:
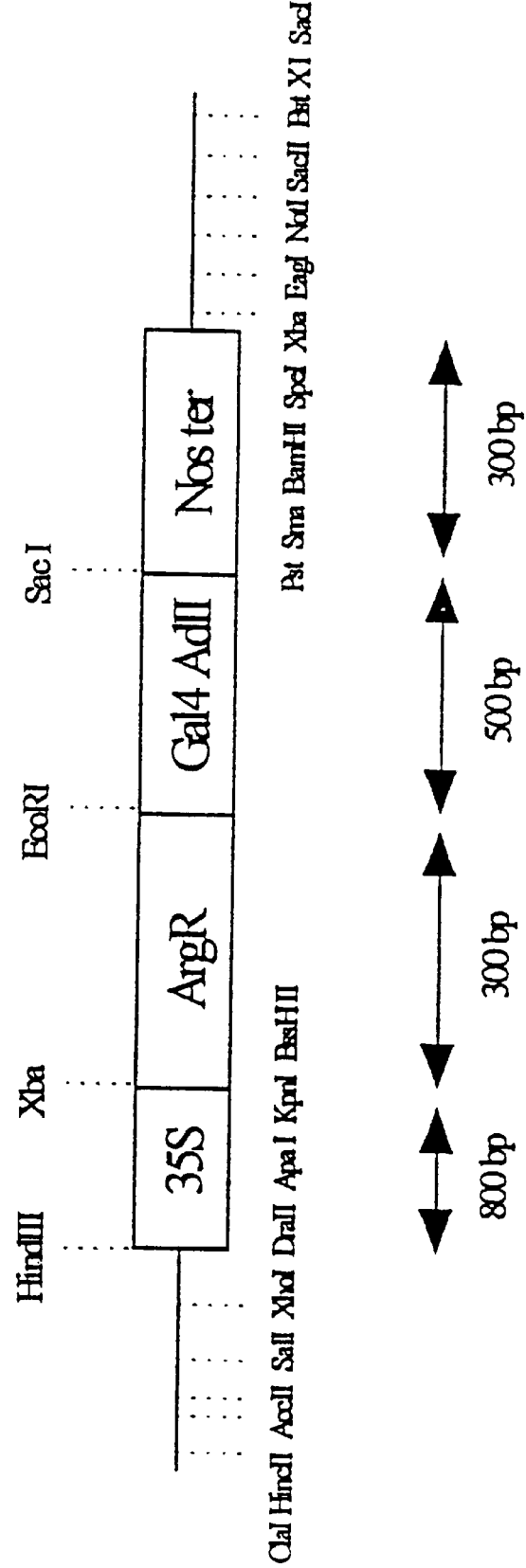
FIG. 6 is a schematic representation of the 35S ArgR Bsc plasmid insert.

FIG. 6 is a schematic representation of the 35S ArgR Bsc plasmid insert.

Figure 7:
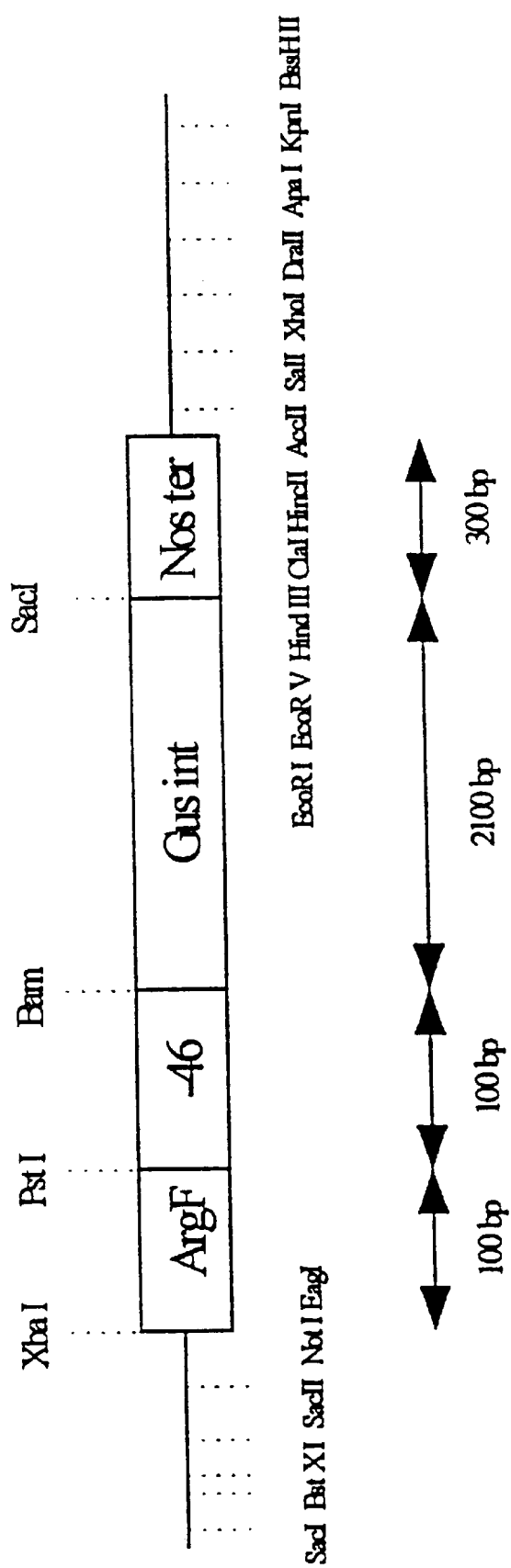
FIG. 7 is a schematic representation of the ArgF-GUS Bsc plasmid insert.

FIG. 7 is a schematic representation of the ArgF-GUS Bsc plasmid insert.

Figure 8:
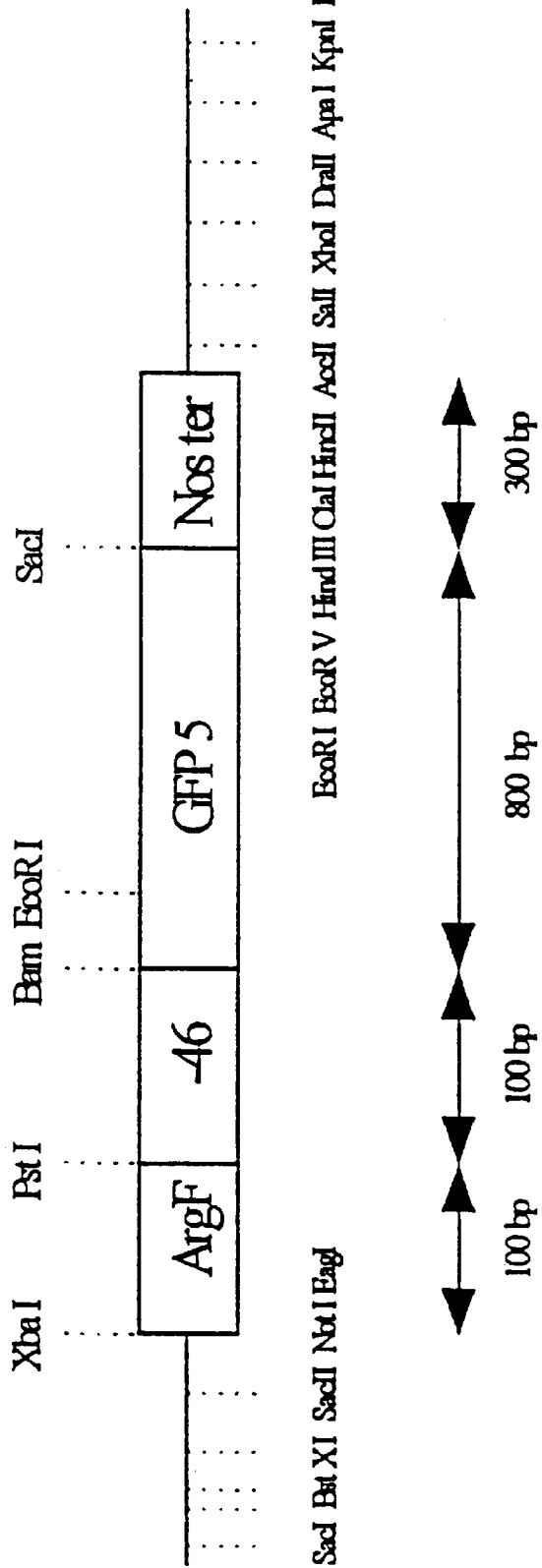
FIG. 8 is a schematic representation of the ArgF-GFP Bsc plasmid insert.

FIG. 8 is a schematic representation of the ArgF-GFP Bsc plasmid insert.

In accordance with one embodiment of the present invention a spatially or temporally regulated promoter can be used to control the expression of a transactivating protein. The expression of the transactivating protein itself the induces the expression of genes having the corresponding UAS element. For example, a seed promoter can be used to control the production of the GAL4 transactivating protein, which in turn activates a UAS sequence attached to each gene. A major advantage of this is shown in FIG. 2 which shows a separate seed regulator plant line being crossed with a target cell line to produce regulated target genes in the F1 hybrids produced.

EXAMPLE 1

Tobacco Cells

In order to demonstrate the ability of GAL4 derivative to transactivate a transgene in plants, the following experiments were undertaken in tobacco cells:

Plasmid Constructions

All DNA constructions were performed using standard procedures as shown in Maniatis et al, (Molecular Cloning: A laboratory manual, 2nd edition, Cold Spring Harbour Laboratory Press (1989)).

Effector Plasmid pMA562, which contains a GAL4 derivative bearing GAL4 (1-147) and ARII was provided by Jun Ma and is disclosed in Ma et al, (Nature, vol. 334, pages 631–633 (1988)). For the construction of pGAL4 the 900 bp GAL4 (1-147)+ARII fragment was excised by partial digestion of pMA582 with Sau3A and inserted into the BamHI site of pUC19 (Yannisch-Perron et al, Gene, Vol. 33, pages 103–119 (1985)) creating pMB1. The 900 bp XbaI-SacI GAL4(1-147)+ARII fragment from pMBI was inserted into the XbaI-SacI cut binary vector pBI-121 (Jefferson et al, EMBO J, Vol. 6, pages 3901–3907, (1987)) downstream of the constitutively expressed 35S Cauliflower mosaic virus (CaMV) promoter (Odell et al, Nature, Vol. 313, pages 810–812) and upstream of the nopaline synthase (NOS) terminator of Agrobacterium tumefaciens, generating pGAL4.

A schematic representation of pGAL 4 is shown in FIG. 3a. This illustrates the position of the CaMV35S promoter, GAL4) insert and NOS terminator in relation to restriction endonuclease sites. FIG. 3b) shows the GAL4 insert and the relationship of the DNA binding and region II activator sequences. The DNA sequence of the insert is represented by SEQ ID NO: 1.

Reporter plasmids

A summary of the production of the reporter plasmids used is shown in FIG. 4. The numbers in brackets are Genbank accession numbers, where these have not been available source journal references have been provided.

pUC19 220.5, which contains constitutively expressed 35SCaMV promoter and the NOS terminator, and CaMV35s GusINTBs, which contains the reporter gene β-glucuronidase, were provided by Robert Shields, PBI, Cambridge.

pNR1 was generated by excising the 2.1 Kb Bam H1-Sac1 GUSint fragment (Vanamneyt et al, Mol. Gen. Genet., Vol. 220, pages 245–250 (1990)) from CaMV35s Gus INT Bs, and inserting this into BamH1-Sac1 cut pUC19 220.5, as shown in FIG. 5a. This shows the relationship of the 35S promoter with the GUSint reporter gene and the termination sequence (Ter).

pNR2, a derivative of pNR1, contains the reporter gene GUSint under the control of the 46S CaMV minimal promoter. The 70 bp-46S CaMV minimal promoter was obtained by PCR, using FIG. s which delineate the 46S CaMV minimal promoter and contain PstI and BamHI sites at their 5' and 3' ends respectively. The 70 bp fragment obtained was inserted into Pst1-BamH1 cut pNR1 (see FIG. 5b).

pUMIGIT, a derivative of pNR2 contains the reporter gene GUSint under the control of the 46S CaMV minimal promoter and 10 synthetic 17bp GAL4 binding sites. The GAL4 binding sites were excised from pMA558 (provided by Jun Ma) as a 170bp BamH1-Sac1 fragment and inserted into BamH1-Sac1 cut Bluescript (Trademark, Stratagene Ltd, Cambridge, UK) generating pNR7. The 2.4 Kb 46S GUSint-NOSter fragment was excised from pNR2 by Pst1-EcoR1 digestion and cloned into Pst1-EcoR1 cut pNR7 thereby generating pUMIGIT (see FIG. 5c).

The sequence of the UAS-GUS construct in pUMIGIT is represented by SEQ ID NO: 2, a schematic representation is shown in FIG. 5d and the complete sequence of pUMIGIT is represented by SEQ ID NO: 3.

pBI-221 is comprised of CaMV35S promoter—GUS-NOS-ter pBI-121 (Jefferson et al, EMBO J; Vol. 6, pages 3701–3907 (1987)) cloned into pUC19 (Yannisch-Perron et al, supra) and was obtained from Robert Shields, PBI Cambridge. This is shown in FIG. 5e.

Large scale plasmid preparation

Large scale plasmid preparation was carried out on $CsCl_2$ gradients (Maniatis et al., Supra).

Plant Material

Tobacco suspension cells were obtained from Jean Evans, PBI Cambridge.

DNA/microprojectile preparation and bombardment conditions 60 mg of tungsten (1 $\mu$m diameter) particles were sterilised in 1 ml 96% ethanol for 5 minutes. During this period the suspension was vortexed. After washing with sterile water, particles were resuspended in 1 ml sterile water. 2.5 $\mu$g of each pNR1, pNR2 pNR8, pGAL4 and pBI-221 were precipitated onto the tungsten particles according to Sanford et al (Meth. Enzymol. Vol. 217, pages 483–509, (1993)). Particle bombardment of tobacco protoplasts was carried out using a helium-driven particle infiltration gun (PIG, Finer et al., Plant Cell Rep. Vol 11, pages 323–328, (1992)).

Histochemical Assay

Transient expression of the uidA gene for β-glucuronidase (GUS) was visualised by staining in 1 mM 5-bromo-4-chloro-3-indolyl β-D-glucuronic acid (X-gluc Sigma, Poole, UK) as described by Jefferson et al., EMBO. J., Vol. 6, pages 3901–3907 (1987)).

Results and discussion

To initially demonstrate the GAL4 that can direct transcription of a UAS-linked reporter gene the following plasmids were introduced into tobacco cells using microprojectile bombardment:

| | | |
|---|---|---|
| a) pNR1 | (35S-GUSint-NOSter) positive control | |
| b) pNR2 | (-46S-GUSint-NOSter) negative control | |
| c) pUMIGIT | (UAS-46S-GUSint-NOSter) reporter construct | |
| d) pGAL4 | (35S-GAL4-NOSter) effector construct. | |

A transient expression assay was utilised to achieve this aim, using microprojectile bombardment to introduce the test and control plasmids into tobacco suspension cells.

pBI-22 1, a plasmid construct known to express GUS in plant cells (Jefferson et al., Supra) acted as an internal positive control in these experiments. 48 h following particle bombardment the tobacco suspension cells were stained for GUS expression by colorimetric assay.

pNRI also gave rise to transient GUS expression 48 h following particle bombardment. The level to which transient reporter gene expression was observed with pNRI was only 40% of that observed using pBI-221 possibly as a result of inefficient intron processing. This result contrasts with the results of Vanamneyt et al, Mol. Gen. Genet. Vol. 220, page 445–250, (1990) who observed no difference between the levels of GUS activity from reporter plasmids bearing the β-glucuronidase gene with and without the intron in plant cells.

The –46S minimal CaMV promoter is unable to direct transcription of linked genes in plants due to the absence of upstream regulatory elements (Odell et al., Supra). Particle bombardment of tobacco cells with pNR2 did not, as would be expected, result in any detectable reporter gene expression.

In order to ascertain that no endogenous plant factor was capable of binding to the UAS and directing expression of the UAS-linked reporter gene, PUMIGIT, was transferred into tobacco suspension cells in the absence of the GAL4 regulator plasmid. No GUS activity could be detected in cells containing this construct alone.

When tobacco protoplasts were bombarded with pUMIGIT and pGAL4 GUS staining was observed. Enzyme activity could not be detected 48 hours following bombardment but, could be detected 7 days post-bombardment. The number of transfection events obtained (GUS-expressing cells identified as blue spots) was equivalent to the number obtained 48 h following bombardment with pNR1. The length of time required before enzyme activity could be detected under these circumstances probably reflects the requirement for two consecutive transcription and translation events to occur before the report gene is expressed.

To ensure that binding of GAL4 to the UAS is responsible for the observed reporter gene activity pGAL4, pNR2 and pGAL4 were transferred into tobacco suspension cells. No GUS staining could be detected in the suspension cells after 7 days of incubation with X-gluc.

These experiments illustrate that the constructs designed to develop the binary system in *Arabidopsis thaliana* and *Brassica napus* function in tobacco suspension cells.

Transactivation in Arabidopsis Plants

In a later experiment DNA comprising UAS-GUS-Ter linked to a hygromycin resistance gene and 35S-GAL4-Ter linked to a kanamycin resistance gene were each put in T-DNA vectors and co-transfected into Arabidopsis roots using Agrobacterium.

Co-transfected root cells were selected using hygromycin and kanamycin and grown into calli. Leaves produced from the calli were then stained for GUS production using X-gluc.

The stained veins of the leaf showed the successful transactivation of the UAS-GUS reporter gene by GAL4 in the Arabidopsis plant.

EXAMPLE 2

Development of the ArgR Transactivation System

The ArgR DNA binding domain was obtained by PCR using primers 5'ARGR (GCTCTAGAAACAATGCGAAGCTCGGCTAAG, SEQ ID NO: 5) and 3'ARGR (GGAATTCGACAACTGCATCGTTGTA, SEQ ID NO: 6) using *E. coli* as a template. The protocol used is described in Innis M. A. et al. PCR Protocols: A Guide to Methods and Applications, Academic Press, San Diego Calif. (1990). The specific conditions were 35 cycles of 94° C. 15 seconds/53° C. 15 seconds/72° C. 15 seconds and 10 minutes 72° C.

The DNA produced was cloned into p35SGAL4, replacing GAL4 DNA binding domain, to produce 35S ArgR Bsc, using XbaI and EcoRi as restriction enzymes. The final construct is shown schematically in FIG. 6.

The DNA sequence of the ArgR DNA binding and GAL4 activation domain II is shown as SEQ ID NO: 4:

5'GCTCTAGAAACAATGCGAAGCTCGGCTAAGCAAG
AAGAACTAGTTAAAG
CATTTAAAGCATTACTTAAAGAAGAG
AAATTTAGCTCCCAGGGCGAAATCG
TCGCCGCGTTGCAGGAGCAAGGCTTT
GACAATATTAATCAGTCTAAAGTCT
CGCGGATGTTGACCAAGTTTGGTGCT
GTACGTACACGCAATGCCAAAATGG
AAATGGTTTACTGCCTGCCAGCTGAA
CTGGGTGTACCAACCACCTCCAGTC
CATTGAAGAATCTGGTGCTGGATATC
GACTACAACGATGCAGTTGTCGAAT TCGCCAATTT-
TAATCAAAGTGGGAATATTGCTGAT-
AGCTCATTGTCCTTCA CTTTCACTACAGTAG-
CAACGGTCCGAACCTCATAACAACTCAAACAAATTC
TCAAGCGCTTTCACAACCAATTGCCTC-
CTCTAACGTTCATGATAACTTCATG AATAATGAAAT-
CACGGCTAGTAAAATTGATGATGG-
TAATAATTCAAAACCA
CTGCACCTGGTTGGACGGACCAAACT-
GCGTATACGCGTTTGGAATCACTAC GGATGTT-
TAATACCACTACAATGGATGATG-
TATATAACTATCTATTCGTGA
TGAAGATACCCCACCAAACCCAAAAAAA-
GAGTAAAATGAATCGTAGATAC TGAAAAACCCCG-
CAAGTTCACTTCAACTGTGCATCGTG-
CACCATCTAATTT
CTTTCATTTATACATCGTTTTGCCT-
TCTTTTATGTAACTATACTCCTCTAAGT TTCAATCT-
TGGCCATGTAACCTCTGATC 3'
(Sequence of ArgR is underlined)

The construct was then subcloned into a Mog 22 binary (commercially available from MOGEN Laboratories) and introduced into *Agrobacterium tumefaciens* C58 (Zambryski P. et al EMBO, 1983, 2, 2143) by electroporation. This was then used to transform *Arabidopsis thaliana* ecotype Wassilewskija (WS) (available from Arabidopsis Stockcentre, Nottingham, UK) by Vacuum infiltration (Hollier P., C. R. Acad Sci Life Sciences, 1995, 318, 465–74). Plants were then selected using hygromycin.

Construction of ArgF GUS lines

Part of the ArgF promoter (Genbank V00 260) was obtained by PCR, using the methodology described above, using the primers
5'ArgF (5'GCTCTAGAATTGTGAAATGGGGT 3', SEQ ID NO: 7) and
3'ArgF (5'GCCTGCAGCGCATGGCGAACGCCACT 3', SEQ ID NO: 8) and *E. coli* as a template.

The product was cloned into –46 -GUS as an Xba/Pst fragment to produce pArgF-GUS Bsc (shown schematically in FIG. 7).

This was then subcloned into Mog 402 binary (Mogen Laboratories) and electroporated into *Agrobacterium tumefaciers* C58. This was then used to transform *Arabidopsis thaliana* ecotype Wassileuskija (WS) by vacuum infiltration. Plants were selected by Kanamycin.

The sequence of the ArgF promoter used (SEQ ID NO: 9) is shown below:
GCTCTAGAATTGTGAAATGGGGTTGCA
AATGAATAATTACACATATAA
AGTGAATTTTAATTCAATAAGTGGCGTTCGCCATG
CGCTGCAGGC
(Sequence of ARG boxes underlined).

Construction of Arg FGFP lines

The GFP gene (Becker, et al, Plant Molecular Biology, 1992, 20: 1195–1197) was cloned into pArgF GUS, replacing the GUS gene to make pArgFGFP. The construct was then subcloned into pGPTV Kan binary and transformed into *Agrobacterium tunefaciens* C58 by electroporation. This was then used to transform *Arabidopsis thaliana* Wassilewskija (WS) by vacuum infiltration. Plants were selected using Kanamycin.

The ArgFGFP Bsc construct is shown schematically in FIG. 8. GFP (Green Fluorescent Protein) fluoresces upon exposure to ultra-violet light allowing its presence to be easily tested.

Transactivation by ArgR

SArgR containing *A. thaliana* lines were crossed with ArgFGUS lines. The progeny of the cross were stained for GUS activity using 5-Bromo-4-chloro-3-indoyl-B-D-glucoronic acid (X-Gluc).

Photographs of the plants showed blue staining indicative of GUS transactivation by ArgR.

EXAMPLE 3

Demonstration of multigene expression

Multigene transactivation may be demonstrated by crossing the progeny of the cross between 35SArgR and ArgF-GUS with *A. thaliana* containing ArgFGFP.

GUS activity may be detected using X-Gluc as discussed above. GFP activity may be detected by exposing the progeny to ultra-violet light.

Such an experiment may be used to demonstrate the expression of GUS and GFP under coordinate control of a single transactivator protein source. In this particular case directed from a single 35S promoter driven ArgR transgene.

Multigene transactivation may also be demonstrated using a transactivator driven by a promoter with a restricted expression pattern such as Scarecrow (Scr). The Scr promoter is disclosed by Malamy, The Plant Journal, 1997, 12 (4), 957–963.

What is claimed is:

1. A method of producing a plant exhibiting one or more desired phenotypic traits, wherein the improvement comprises the steps of:
   (i) providing a first and a second transgenic plant;
   (ii) pollinating the first transgenic plant with pollen from the second transgenic plant to produce an embryo or seed, wherein:
      one of the transgenic plants comprises at least [one] two nucleic acid sequences, each nucleic acid sequence encoding for a phenotypic trait selected from the group consisting of herbicide resistance, the production of a polyhydroxyalkanoate male sterility, antisense RNA mediated inhibition of target mRNAs or sense RNA inhibition of mRNAs, wherein each nucleic acid sequence encoding for a phenotypic trait is operatively linked to a separate upstream activating sequence recognition site; and
      the other transgenic plant comprises a nucleic acid sequence encoding a promoter operatively linked to a nucleic acid sequence encoding for a transactivating protein which activates each of the upstream activating sequences; and
   (iii) growing the embryo or seed into a plant.

2. A method according to claim 1, wherein the first transgenic plant is male sterile.

3. A plant produced by the method of claim 1, wherein the polyhydroxyalkanoate is polyhydroxybutyrate.

4. A method according to claim 1 wherein male sterility is controlled by nucleic acid sequences comprising the ribonuclease barnase and its inhibitory subunit barstar.

5. A method according to claim 1, wherein the mRNA inhibited is polygalactonuronidase or ACC oxidase.

6. A method according to claim 1, wherein the plant produced is selected from the group consisting of blackberry, apple, pear, plum, cherry, raspberry, strawberry, damson, tobacco, potato, barley, rice, legume, wheat, Brassica, and Arabidopsis.

7. A method according to claim 1, wherein the plant produced is selected from the group consisting of sunflower, canola, soybean and oilseed rape.

8. A method according to claim 1, wherein the transactivating protein comprises the ArgR DNA binding domain.

9. A method according to claim 1, wherein the upstream activating sequence is the sequence within plasmid ArgF-GUS Bsc.

10. A method according to claim 1, wherein the desired phenotypic trait is expressed in a tissue specific manner.

11. A method of producing plant reproductive material, wherein the improvement comprises the steps of:
   (i) providing a first and a second transgenic plant; and
   (ii) pollinating the first transgenic plant with genetic material from the second transgenic plant to produce an embryo or seed, wherein:
      one of the transgenic plants comprises at least two nucleic acid sequences, each nucleic acid sequence encoding for a phenotypic trait selected from the group consisting of herbicide resistance, the production of polyhydroxyalkanoate male sterility, antisense RNA mediated inhibition of target mRNAs or sense RNA inhibition of mRNAs, wherein each nucleic acid sequence encoding for a phenotypic trait is operatively linked to a separate upstream activating sequence recognition site; and
      the other transgenic plant comprises a nucleic acid sequence encoding a promoter operatively linked to a nucleic acid sequence encoding for a transactivating protein which activates each of the upstream activating sequences.

12. A method according to claim 11, wherein the first transgenic plant is male sterile.

13. The method of claim 11, wherein the polyhydroxyalkanoate is polyhydroxybutyrate.

14. A method according to claim 11 wherein male sterility is controlled by nucleic acid sequences comprising the ribonuclease barnase and its inhibitory subunit barstar.

15. A method according to claim 11, wherein the mRNA inhibited is polygalactonuronidase or ACC oxidase.

16. A method according to claim 11, wherein the transgenic plants are selected from the group consisting of blackberry, apple, pear, plum, cherry, raspberry, strawberry, damson, tobacco, potato, barley, rice, legume, wheat, Brassica, and Arabidopsis.

17. A method according to claim 11, wherein the transgenic plants are selected from the group consisting of sunflower, oilseed rape, canola and soybean.

18. A method according to claim 11, wherein the transactivating protein comprises the ArgR DNA binding domain.

19. A method according to claim 11, wherein the upstream activating sequence is the sequence within plasmid ArgF-GUS Bsc.

20. A method according to claim 11, wherein the nucleic acid sequence(s) encoding the desired phenotypic trait is additionally operatively linked to a tissue specific promoter.

21. A method of controlling two or more genes in a plant, wherein the improvement comprises the steps of inserting into a plant:
   (i) two or more exogenous genes, each of which is operatively linked to a nucleic acid sequence encoding for a heterologous upstream activating sequence recognition site; and
   (ii) a nucleic acid sequence encoding for a promoter operatively linked to a nucleic acid sequence encoding for a transactivating protein which is capable of activating the upstream activating sequence.

22. A method according to claim 21, wherein the plant is selected from the group consisting of blackberry, apple, pear, plum, cherry, raspberry, strawberry, damson, tobacco, potato, barley, rice, legume, wheat, Brassica, and Arabidopsis.

23. A method according to claim 21, wherein the plant is selected from the group consisting of sunflower, oilseed rape, canola and soybean.

24. A method according to claim 21, wherein the exogenous genes encode for the production of a polyhydroxyalkanoate, such a polyhydroxybutyrate.

25. A method according to claim 21 wherein the two or more exogenous genes encode for a male sterility phenotypic trait.

26. A method according to claim 25 wherein the two or more exogenous genes encode for the ribonuclease barnase and its inhibitory subunit barstar.

27. A method according to claim 21 wherein the two or more exogenous genes encode for antisense RNA or sense RNA inhibition of target genes.

28. A method according to claim 21, wherein the transactivating protein comprises the ArgR DNA binding domain.

29. A method according to claim 21, wherein the upstream activating sequence is the sequence within plasmid ArgF-GUS Bsc.

30. A method according to claim 21, wherein one or more of the exogenous genes are additionally operatively linked to tissue specific promoters.

31. Use of a protein comprising the DNA binding site of ArgR to regulate transcription of a nucleic acid molecule in a plant.

32. An isolated nucleic acid molecule encoding the ArgR DNA domain operably linked to the GAL4 activation domain II.

* * * * *

UNITED STATES PATENT AND TRADEMARK OFFICE
CERTIFICATE OF CORRECTION

PATENT NO.     : 6,127,606
DATED          : October 3, 2000
INVENTOR(S)    : Malcolm Bennett, et al.

It is certified that error appears in the above-identified patent and that said Letters Patent is hereby corrected as shown below:

<u>Claim 1, column 25,</u>
Line 40, delete "[one]".

Signed and Sealed this

Second Day of October, 2001

*Attest:*

*Nicholas P. Godici*

*Attesting Officer*

NICHOLAS P. GODICI
*Acting Director of the United States Patent and Trademark Office*